United States Patent [19]

Burt et al.

[11] Patent Number: 5,525,621
[45] Date of Patent: Jun. 11, 1996

[54] IMIDAZOLE DERIVATIVES AS PROTECTIVE AGENTS IN REPERFUSION INJURY AND SEVERE INFLAMMATORY RESPONSES

[75] Inventors: Stanley Burt, Middletown; Jack R. Collins, Frederick, both of Md.

[73] Assignee: Cytos Pharmaceuticals LLC, Durham, N.C.

[21] Appl. No.: 246,419

[22] Filed: May 20, 1994

[51] Int. Cl.⁶ ..................................................... C07D 49/36
[52] U.S. Cl. ........................ 514/393; 514/397; 548/312.7; 548/302.1
[58] Field of Search ..................... 514/393, 397; 548/312.7, 302.1

[56] References Cited

FOREIGN PATENT DOCUMENTS 1341375  12/1973  United Kingdom ........... C07D 49/36
93/14070  7/1994  WIPO ........................ C07D 233/64

*Primary Examiner*—Jacqueline Haley
*Attorney, Agent, or Firm*—Isaac A. Angres; Susan Petraglia

[57] ABSTRACT

Compounds of the formula

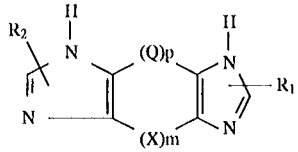

wherein the substituents are as defined in the disclosure. The compounds are particularly useful for inhibiting damage to a variety of mammalian tissue that are jeopardized, for example, during runaway inflammatory conditions due to the damaging presence of singlet oxygen, the hydroxyl radical, cytokines and growth factors. The compounds are also useful in inhibiting damage to cardiac and central nervous system tissues during reperfusion.

53 Claims, No Drawings

IMIDAZOLE DERIVATIVES AS PROTECTIVE AGENTS IN REPERFUSION INJURY AND SEVERE INFLAMMATORY RESPONSES

FIELD OF THE INVENTION

The present invention generally relates to preventing or ameliorating tissue damage that occurs during ischemia/reperfusion conditions, and from cytokine, growth factor, and chemotactic cascades that arise during severe inflammatory conditions. More particularly, the invention is related to the use of certain imidazole derivatives as protective agents for conditions such as acute myocardial infarction, stroke, spinal cord injury, head injury, severe infectious diseases, inflammatory bowel conditions, cancer treatment, and numerous surgical procedures.

The present invention further relates more generally to the protection of various types of tissue whenever the inflammatory condition involves the damaging effects of oxygen free radicals and oxygen intermediates, and cytokines and growth factors which are involved in "runaway" inflammatory conditions. Hence the invention also relates to methods of treating various tissue types from mammalian species against the damaging effects of singlet oxygen, hydroxyl radical, cytokines and growth factors using certain imidazole derivatives discovered by the inventors.

The invention also relates to methods for improving post-ischemic myocardial and neuronal tissue functions in mammalian species by administering certain imidazole derivatives.

In another aspect of the invention, the imidazole derivatives can be combined with thrombolytic agents, anti-coagulants, antisense nucleotides, steroidals, and other compounds.

BACKGROUND OF THE INVENTION

Oxygen free radicals and oxygen intermediates, especially singlet oxygen and the hydroxyl radical, cause extensive tissue damage. Free radicals and oxygen intermediates within living cells arise from endogenous sources, for example, from mitochondrial electron transport chain, oxidant enzymes, phagocytic cells and auto-oxidation reactions, as well as from exogenous sources such as cigarette smoke, "redox cycling" drugs and pesticides, heat stress, and ionizing radiation. These oxygen species damage compounds of all biochemical classes, including nucleic acids, protein and free amino acids, lipids and lipoproteins, carbohydrates, and connective tissue macromolecules. In addition, these oxygen species are believed to have an impact on cellular activities, such as membrane function, metabolism, and gene expression. Both singlet oxygen and hydroxyl radical are known to produce damaging strand breaks in DNA during reperfusion (specifically, during the reoxygenation aspect of reperfusion following ischemia) and during severe inflammatory conditions. Also, these oxidants, in the presence of metal ions (e.g., iron), initiate lipid peroxidation, which, in turn, produces mutagens, carcinogens, and other reactive oxygen species.

Numerous clinical conditions implicate oxygen radicals as the cause of tissue damage in single organs such as erythrocytes (e.g., lead poisoning), lungs (e.g., acute respiratory distress syndrome), heart and cardiovascular system (e.g., atherosclerosis), kidney (aminoglycoside nephrotoxicity). GI tract (e.g., free-fatty-acid-induced pancreatitis), brain and CNS (e.g., senile dimenti, hypertensive cerebrovascular injury, and cerebral trauma), eye (e.g., cataractogenesis), and skin (e.g., solar radiation and contact dermatitis.) Clinical conditions involving multiorgan disorders linked to oxygen radicals include, for example, inflammatory-immune injury, ischemiare-flow states, radiation injury, aging, cancer and amyloid diseases.

In spite of the more recently known deleterious effects of these oxygen species, the scientific community has focused its attention on the superoxide anion for the past two decades, leaving largely unexplored the role of singlet oxygen and the hydroxyl radical in human disease. Thus, no drugs that specifically target these oxygen species are currently available. It is one of the goals of the present invention to design a series of drugs that can scavenge or neutralize singlet oxygen and the hydroxyl radical in tissue experiencing oxidative stress. In particular, the need for such drugs is particularly great for protecting or treating cardiac tissue undergoing heart attack, angioplasty, and cardiac surgery. The invention also addresses the need for ameliorative drug therapies for ischemic stroke, vasospasm during subarachnoid hemorrhage, head injury, spinal cord injury, and neurosurgery, whereby the effects of free radical damage from reperfusion and inflammation would be prevented or lessened.

Another aspect of the invention is the control of tissue damage caused by the presence of cytokines and growth factors during severe inflammatory conditions (a.k.a. runaway inflammatory conditions) and by chemotactic cascades caused by surgical intervention, infectious diseases, parasitic and other inflammatory conditions. It is believed that cytokines are responsible for "communication" between cells which ultimately leads to gene activation. These discrete signaling molecules are considered benign to tissue in a healthy state. Cytokines include interleukins, various growth factors, interferons, and colony-stimulating factors. However, the net biological effect of the interaction of this class of molecules can also be inflammation and in this instance, cytokines are also known to play a major role in a wide variety of disease states such as cancer, allergy, infection, inflammation, angiogenesis, and differentiation. Cytokines and growth factors together are also believed to play a major role in restenosis (neointimal hyperplasia or proliferation following percutaneous transluminal coronary angioplasty and related procedures for removing blockages within blood vessels and lymph ducts).

The mechanism by which tissue is damaged during a runaway inflammatory response caused, for example, by a bacterial infection is as follows. Inflammatory cytokines such as tumor necrosis factor and interleukin-1 activate intracellular, microbicidal neutrophils. In their normal, defensive operation, neutrophils aggregate and release toxic granule proteins and the products of neutrophil oxidative burst to destroy the harmful microbe. However, in a runaway process, the neutrophil aggregation and release of microbicidal substances are not localized in the vicinity of the microbe, leading to damage of the host tissue. This chain of events occurs in a number of diseases associated with, e.g., infectious agents the immune system, chronic inflammation, and the respiratory system, as well as during numerous surgical procedures.

Accordingly it is another goal of the invention to design a series of drugs that can ameliorate tissue damaged by severe inflammatory responses, without interfering with host tissue defense mechanisms. In particular, the invention recognizes the great need for ameliorative drug therapies for stroke, heart attack, restenosis, adult respiratory distress syndrome (ARDS) and septic shock (the latter two conditions having a high likelihood of fatality), asthma, hearing loss associated with bacterial meningitis, inflammatory bowel conditions, and dozens of other conditions.

Blood flow reductions in the heart can result in dysfunction of this organ and cell death if the flow reduction is severe enough. Restoration of coronary blood flow early during a heart attack is becoming a clinical reality with the advent and improvements in thrombolytic, mechanical, and surgical interventions. While early restoration of blood flow by thrombolysis or following transient ischemia can prevent or mitigate the degree of cell death (infarction), reperfusion can still result in some degree of cardiac dysfunction or cell death (also referred to as stunned myocardia). Thus, it would be of great clinical value to find a means to preserve normal function of the heart during reperfusion and during various forms of cardiac surgery.

Additionally, heart disease is the biggest cause of death in the Western world. There are many different forms of heart disease and disease states can develop from a number of different factors including stress, diet, tobacco use, and genetic make up of the individual. Ischemia is a heart disease condition characterized as a local hypoxia caused by mechanical obstruction or occlusion of the blood supply. Oxygen radicals have been implicated as important mediators of tissue injury during myocardial ischemia and reperfusion. A number of studies have shown that free radicals, particularly superoxide anions ($O_2-$) and hydroxyl radicals are generated following reperfusion of the ischemic myocardium and have linked the free radical generation to the loss of contractile function. Superoxide anion is relatively unreactive and is considered dangerous because its dismutation results in the formation of hydrogen peroxide which can potentially generate the highly reactive hydroxyl radical (OH) in the presence of transition metal ions. It is therefore generally believed that ultimate tissue damage occurs due to OH radicals. Indirect proof for the involvement of OH radicals in ischemia/reperfusion injury is derived from observations of a protective effect of OH radical scavengers such as dimethylthiourea (DMTU), dimethylsulfoxide, and mannitol. In addition, certain agents which prevent the formation of hydroxyl radicals have also demonstrated a protective effect, including deferoxamine, superoxide dismutase, and catalase.

Another active oxygen species is singlet molecular oxygen ($^1O_2$). Singlet oxygen is not a radical; rather, it is an electronically excited state of oxygen which results from the promotion of an electron to higher energy orbitals. In Kukreja et al., *Biochim. Biophys. A*, 990:198–205 (1990), and Kukreja et al., *Am. J. Physiol.*, 259:H1330-H1336 (1989), data was presented which demonstrated that superoxide anion or hydrogen peroxide are the least reactive species in damaging sarcolemma or sarooplasmic reticulum. Therefore, it might be inferred that the only species believed to be injurious in myocardial tissue is OH radical can initiate lipid peroxidation which can produce lipid free radicals that may become important sources of singlet oxygen in vivo. Hence, the damage often attributed to the OH radical could be the resultant effects of other intermediate reaction products, including lipid free radicals and singlet oxygen.

Janero et al., J. Mol. Cell Cardiol., 21:1111–1124 (1989), showed that α-tocopherol provides cellular protection by acting as a chain breaker in the lipid peroxidation process, not by scavenging the $O_2-$ radical per se. Singlet oxygen is also acted upon by α-tocopherol. Hearse et al., *Circ. Res.*, 65:146–153 (1989), and Vandeplassche et al., J. Mol. Cell Cardiol., 22:287–301 (1990) (abstract) showed that $^1O_2$ generated from exogenous sources is able to mimic ischemia/reperfusion induced myocardial damage. Tarr et al., *J. Mol. Cell Cardiol.*, 21:539–543 (1989), recently reported that rose bengal, when applied extracellularly to frog atrial myocytes, induced a prolongation followed by a reduction of action potential duration. In addition, Donck et al., *J. Mol. Cell Cardiol.* 20:811–823 (1988) reported that isolated myocytes exposed to rose bengal light rapidly experience ultrastructural injury.

In Kukreja et al., *Abs. of 63rd Sci. Sess. (AHA) (Dallas)*, 1068 (1990), it was reported that singlet oxygen generated from photosensitization of rose bengal induced significant inhibition of calcium uptake and $Ca^{2+}$—ATPase activity in isolated sarcoplasmic reticulum. This damage caused by singlet oxygen could be significantly reduced using L-histidine, but not with SOD or catalase. Misra et al., *J. Biol. Chem.*, 265-15371–15374 (1990), reported that L-histidine is a scavenger of singlet oxygen. In contrast, SOD and catalase are scavengers of superoxide anion. Kim et al., *Am. J. Physiol.*, 252:H252–H257 (1987), demonstrated that L-histidine provides significant protection of sarcolemmal $Na^+K^+$—ATPase activity following ischemia/reperfusion in guinea pig hearts.

Electrocardiography is a well known technique for examining the condition of the heart. There are four chambers in the human heart. In operation, the right atrium receives venous blood from the body and pumps it into the right ventricle which pumps the blood through the pulmonary network where the blood becomes oxygenated by the lungs. The oxygenated blood is returned to the left atrium and is pumped into the left ventricle. The left ventricle is the most powerful chamber of the heart and serves the function of propelling the blood throughout the body network. Typically, 2,000 gallons of blood a day are pumped through the heart of a normal individual, and the heart keeps this pace throughout the life of the individual (e.g., seventy years or more). An electrocardiograph apparatus enables doctors to monitor electrical changes in the heart muscle. All the functions of the body are motivated by a complex electromechanical system which is controlled through the brain and central nervous system. Each cell within the body is surrounded by a membrane which is electrically "polarized", meaning they each have positive and negative ions on opposite sides of the membrane. Contraction of a heart muscle cell causes an electrical current flow due to the positive and negative ions. Because all of the heart cells are intimately connected, the head organ acts as one very large cell. In the resting state (diastole), no current flows; however, as the heart expands and contracts, electrical current flows and can be sensed by electrodes.

Electrocardiography is the process of sensing and analyzing the current flow in the heart of a patient. Because the principal current detectable when a patient is at rest is produced by the heart, electrodes need not be connected directly to the heart. Typically, six or more electrodes are positioned on different portions of a patient's chest to sense the electric signals from the heart. The sensed signals are recorded on a monitor or strip chart and are referred to as an electrocardiogram. The electrocardiogram is often referred to as an ECG or EKG. According to a technique developed by William Einthoven in 1901, points on an ECG are labeled according to a PQRSTU system. The P wave represents activity in the artria and the QRST waves represent ventricular activity. The heart's action is triggered by its own built-in pacing mechanism which comprises a bundle of specialized cardiac muscle fibers known as the sino-atrial node. The P wave represents the time taken for the electrical signal to travel throughout the muscle of the atria, whereas the QRS section represents the ventricular muscle being depolarized and the T section represents the ventricular repolarization. The U section is often not detected and its meaning is not precisely known.

The ECG trace can provide several important pieces of information about the heart. One of the most important measurements to be made from the ECG trace is the PR interval. The PR interval is a measure of the time taken for the electrical impulse to travel through the atria to another specialized muscle bundle which synchronizes the actions of the atria and ventricles. Specifically, the PR interval is a recording of the cardiac impulse traveling to the atrioventricular (AV) node and the bundle of His, and then traversing the bundle branches and Purkinje fibers. The PR interval usually lasts 0.12 to 0.21 seconds. A longer period indicates a breakdown in the smooth operation of the AV node. The QRS section should last 0.06 to 0.11 seconds and longer periods typically indicate that the ventricles are acting sluggishly and not getting their electrically impulses simultaneously. The isoelectric ST segment and upright T wave follow the QRS section and represent ventricular repolarization. The ST segment is a sensitive indicator of myocardial ischemia or injury and should be on the isoelectric line.

Arrhythmia is a condition where the heart beats with an irregularity in the force or rhythm. In ventricular tachycardia, there is a rapid and repetitive firing of premature ventricular contractions. When the ventricles contract rapidly with this arrhythmia, the volume of blood ejected into the circulation is often inadequate. This kind of arrhythmia, if left untreated, often degenerates into fatal ventricular flutter or fibrillation. In ventricular fibrillation, there is no recognizable QRS complex and an extremely irregular rhythm. In this type of arrhythmia, virtually no blood is ejected into the systemic circulation, and death will occur if no corrective action is taken.

A major concern during cardiopulmonary bypass procedures is minimizing ischemic damage to the myocardium, thereby avoiding depressed myocardial performance in the post operative period. Prolonged ischemia such as that following myocardial infarction or occurring during long-term coronary bypass procedures causes serious damage to the myocardium. It has been suggested that free radicals are involved in the patho-physiology of ischemia-induced tissue damage. During ischemia, increased reducing equivalents are produced and this may favor the production of $O_2^-$ anion and other free radical species upon reoxygenation. Many and varied compounds have been reported to reduce the susceptibility of the heart to ischemia/reperfusion injury. These include agents which inhibit free radical production or facilitate their elimination. Other therapeutic agents include calcium channel blockers, prostacyclin analogs and thromboxane inhibitors, sodium channel blockers, and $\alpha$- and $\beta$-adrenergic receptor blockers. Some of these agents are effective against ischemia and reperfusion induced arrhythmia's, whereas others are effective against only one or the other. Prior to this invention, there were no unique, manmade agents available which abolish arrhythmia's, improve contractility, and protect the heart ultrastructurally.

SUMMARY OF THE INVENTION

It is therefore an object of this invention to provide a method of using imidazole derivatives in the treatment of arrhythmia's, including ventricular tachycardia and ventricular fibrillation.

It is also an object of this invention to use imidazole derivatives to protect the ultrastructure of cardiac cells.

Another object of the invention is to control (e.g., prevent or ameliorate) tissue damage caused by severe runaway inflammatory responses and by chemotactic cascades during surgical procedures.

It is yet another object of this invention to provide drugs for use in heart surgery neurosurgery and organ transplantation that contain certain imidazole derivatives for scavenging singlet oxygen and hydroxyl radicals, and other compounds for scavenging superoxide and hydroxyl radicals.

According to the invention, it was hypothesized that singlet oxygen is one of the most destructive species in ischemia/reperfusion injury and that certain imidazole derivatives, because of their singlet oxygen scavenging ability, could be advantageously used for the protection of the heart, central nervous system, and other tissues exposed to attack by singlet oxygen. In vitro and in vivo experiments have been conducted which show that the imidazole derivatives of the present invention have beneficial effects in preventing ischemia/reperfusion induced contractile dysfunction's, arrhythmia's, including tachycardia and ventricular fibrillation, impairment of coronary flow, and ultrastructural damage to a variety of tissues during the severe inflammatory response of tissue.

In applicants' design of L-histidine-like $^1O_2$ and OH-radical scavenger molecules, they have assumed the imidazole ring to be the active pharmacophore for the system. In their computer studies, they have used the model system 4-methyl-imidazole to examine the properties that are most likely responsible for the activity of L-histidine in quenching $^1O_2$ andOH. Based on the reactivity of $^1O_2$ and OH and their affinity to form the superoxide and OH-radicals, applicants make the assumption that the scavenger molecules are serving as an electron source for an electrophilic attack by $^1O_2$ and OH. By analogy with the furans and carotenoids, it appears most likely that the $\pi$ system of the imidazole ring is the feature that must be retained in all design strategies. Further analogy suggests that endoperoxide formation is a viable candidate for the reaction of $^1O_2$ with histidine. Therefore, a small hererocyclic ring system should also be included in the initial design strategy.

Calculations on our model methyl-imidazole system revealed the fact that the two unsubstituted carbon centers are the most electron rich and have the highest density in the highest occupied molecular orbital (HOMO). The orbital structure of the HOMO, based on the canonical orbital representation, indicates that the two carbon centers have opposite phases with respect to each other. This arrangement, geometric, spatial, and phasing, of the orbitals on the two carbon centers is complementary to the attack of $^1O_2$. In $^1O_2$, the electrophilic character is due to the lowest unoccupied molecular orbital (LUMO), which is anti-bonding with the two $\pi$ orbitals possessing opposite phases. Due to the planar ring of the imidazole, the spatial orientation of the pi orbitals of two unsubstituted carbon centers are parallel. This fact, coupled with the geometric distance between the two centers, 2.2A, leads to a stable (58 kcal/mol), optimized, model of $O_2$-imidazole endoperoxide adduct formation with a C—O—O bond angle of 101°. This angle is quite close to the "quasi-tetrahedral" angle in water of 105°. The stability of this complex is easily rationalized by the redistribution of the electronic structure of the $\pi$ orbitals, especially the LUMO, and forming two single bonds and two lone pairs in the final adduct. All of these results are consistent with the general design principles outlined in the previous paragraph. In brief, small unsaturated hererocyclic ring systems that induce significant excess electron density at two carbon centers approximately 2.2A apart and having significant anti-phased contributions to the HOMO should be the most reactive species for endoperoxide formation, resulting in complete destruction of $^1O_2$.

With respect to the OH radical, applicants' have investigated two possible mechanisms for the trapping by the imidazole functional group of histidine. In the first, they investigated the possibility of OH attack on the two unsubstituted carbon centers of our methyl-imidazole model. Each of these led to very stable (54 and 44 kcal/mol) adducts. However, the resulting adducts are also radicals that can further react. Fortunately, these adduct radical species should be less reactive towards lipids and other biologically relevant molecules due to delocalization of the free electron and the electron affinity. These species would probably be reduced to form the anion and subsequently protonated at the free nitrogen lone pair. Again, due to the electrophilic nature of the OH radical, the fundamental design paradigm appears to be excess electron density at the unsubstituted carbon positions of our model. Another possibility that was indicated by applicants' calculations suggests it is possible that a temporary adduct between the OH radical and the lone pair of the nitrogen in the imidazole ring can exist. Initial calculations suggest that this could lead to charge transfer and the formation of an imidazole cation and the OH anion. This process may be favored since there should be no barrier to reaction, resulting in increased reaction kinetics. If this second process is dominant, then the primary feature in the design OH radical scavengers should be the inclusion of a heteroatom with a weakly held lone pair that can interact with the incoming electrophile, OH.

The compounds designed by applicants' have focused on incorporating these general features into new analogues that can mimic the protective reactions of L-histidine. Substitutions that lead to an increased electron buildup on the carbon centers of the imidazole, or analogous rings should increase the efficiency of the scavenging process. In these lines, furans have been included in applicants' considerations of possible lead compounds for therapeutic uses.

DESCRIPTION OF THE PREFERRED EMBODIMENTS

The present invention relates to a compound of the formula:

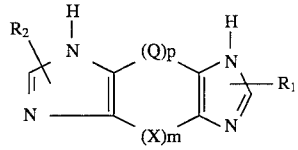

wherein $R_1$ and $R_2$ are selected from the group consisting of hydrogen and normal, secondary, branched and tertiary $C_1$–$C_{18}$ alkyl groups; X is a heteroatom selected from the group consisting of oxygen and sulfur; Q is selected from the group consisting of —$(CH_2)n$—, —$(CH)$—$_n$

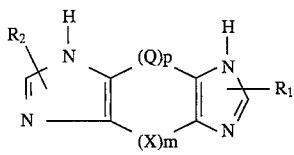, —$(CH_2)_x$—N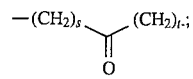N(—$CH_2)_y$ and

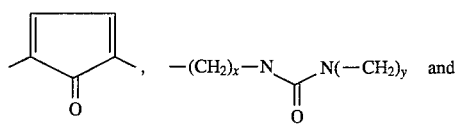

and
m=0 or 1
p=0 or 1
n=1–18
x=y=0–3
s=1–3
t=1–3 with the proviso that when p=0 then m=1 and the imidazole rings are joined together by a single bond to make a fused tricyclic ring, and when m=0 then p=1.

The term —(CH)—$_n$ refers to an alkenyl group having two or more carbon atoms and which is preferably conjugated.

Typical compounds within the scope of the present invention include di(5-imidazolyl methyl) ketone; bis 2,3-4,5 imidazo furan; N,N'-diimidazolyl urea; 2,5-(di-5-imidazolyl) cyclopentadien-1-one, 1,2-di(-5 imidazolyl) ethane, 1,3-di(5-imidazolyl) propane, 1,4-di(5-imidazolyl butane as well as the alkyl substituted derivatives of the above compounds.

The present invention further relates to various methods for inhibiting, treating, or ameliorating reperfusion injury, cardiac abnormalities, cytokine- and growth factor-mediated runaway inflammatory responses, injury from chemotactic cascades, and conditions arising from the deleterious effects of oxidative stress from singlet oxygen and free hydroxyl radical on tissue, in a mammalian organism manifesting at least one of these conditions, said methods comprising administering to said mammal an amount of an imidazole derivative effective in the inhibition, treatment, or amelioration of the above-listed conditions, said imidazole derivative having the formula:

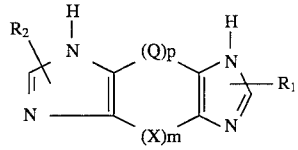

wherein $R_1$ and $R_2$ are selected from the group consisting of hydrogen and normal, secondary, branched and tertiary $C_1$–$C_{18}$ alkyl groups; X is a heteroatom selected from the group consisting of oxygen and sulfur; Q is selected from the group consisting of —$(CH_2)n$—, —$(CH)$—$_n$

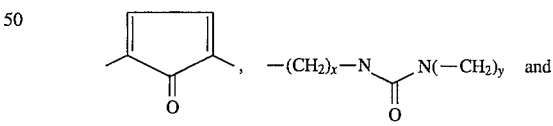

and
m=0 or 1
p=0 or 1
n=1–18
x=y=0–3
s=1–3
t=1–3 with the proviso that when p=0 then m=1 and the imidazole rings are joined together by a single bond to make a fused tricyclic ring, and when m=0 then p=1.

Ventricular fibrillation is corrected with the addition of therapeutic quantities of the imidazole derivative to the heart and the membranes of heart cell ultrastructural components are protected with the addition of the imidazole derivatives. It should be understood that the experimental results reported herein are provided for purposes of example and that other similar imidazole derivatives could be used to achieve the beneficial effects which have been discovered.

In the in vitro experiments, male rats (250–350 gm) of the Sprague-Dawley strain were obtained from Charles River's Breeding Farms of Massachusetts. Throughout the experiments the rats were allowed ad libitum access to standard laboratory stock diet and water. In the perfusion technique, each of the animals was anesthetized with diethyl ether, and thirty seconds later, hearts with a segment of ascending aorta attached, were excised and placed in cold (4° C.) normal saline until contraction ceased (approximately 15 seconds (s)). Each heart was then cannulated through the aorta and perfused according to the method described in Langendroff, *Pfluger Arch. Physiol.*, 61:291–332 (1895), at a constant pressure of 100 cm $H_2O$. The perfusate was a modified Krebs-Henseleit (KH) buffer including the following: NaCl, 118 mM; $CaCl_2$, 2.5 mM; $MgSO_4$, 1.2 mM; $NaHCO_3$, 25 mM; and KCl.

The imidazole derivatives according to the invention are effective in the protection of cells and vessels and tissue of various mammalian organs, inclusive of erythrocytes, lungs, heart and cardiovascular system, kidney, gastrointestinal tract, brain, eye and skin. In most, if not all, of these organs the tissue damage is the result of oxygen radical formation upon the reoxygenation during reperfusion and inflammatory states. Alternatively, the damage may arise from the harmful, runaway interaction by cytokines and growth factors during a normal host defense mechanism of a mammal.

Additionally, experiments have been conducted in vitro and in vivo which show that the imidazole derivatives of the present invention beneficially affect the electrical system of the heart as well as protect structural and ultrastructural components of head cells. Specifically, the arrhythmic conditions of ventricular tachycardia 3.2 mM, $KH_2PO_4$ (1.2 mM) and glucose, 11.1 mM. The perfusate solution was continuously gassed with 95% $O_2$ plus 5% $CO_2$. The pH of the buffer was stable at 7.4. The imidazole derivative was directly dissolved in some of the buffer to create solutions having imidazole derivative final concentrations ranging from 10–50 mM. Some of the buffer was also combined with SOD/catalase/mannitol. All perfusion KH buffers were prepared on the day of the experiment in double-distilled deionized water.

After the excised heads began spontaneous contraction, a small incision was made at the junction of the left atrium with the left ventricle. A latex balloon connected to a pressure transducer via a polyethylene cannula was inserted through the left atrium and mitral valve into the left ventricle. The pressure transducer was connected to a multichannel polygraph (Grass) recorder. The balloon was inflated with water sufficient to raise the end diastolic pressure to 5 mm Hg. Coronary flow was monitored by collecting the effluent from the heart at timed intervals. An electrocardiogram (ECG or EKG) was recorded throughout the experiment via two silver electrodes attached to the ventricular apex and to the aortic cannula. In the experiments, the hearts were perfused with either the modified KH buffer alone or modified KH buffer plus imidazole derivative or SOD/catalase/mannitol. An initial thirty minute period was allowed to equilibrate rhythm and hemodynamics, and this period was followed by ischemia for 30 minutes achieved by clamping the aortic cannula. During the experiment, the heart was enclosed in an air space surrounded by a water jacket at 37° C. Reperfusion of the heart was started by opening the cannula.

In the experiments, ventricular arrhythmia's were defined and quantified in accordance with the Lambeth Conventions described in Walker et al., *Cardiovasc. Res.*, 22:447,455 (1968). High speed ECG recordings were analyzed for the incidence and mean time to onset of ventricular tachycardia and ventricular fibrillation. Ventricular tachycardia was defined as a run of four or more consecutive ventricular premature beats. Ventricular fibrillation was defined as a ventricular rhythm with no recognizable QRS complex, in which signal morphology changed from cycle to cycle, and for which it was impossible to estimate heart rate.

Immediately following reperfusion, hearts with the canula still intact were taken from the Langendorff apparatus and placed in cold saline on ice. The cannula was then fitted to a perfusion pump and 1% glutaraldehyde and 1½% paraformaldehyde in 0.1M Na cacodylate at pH 7.4 was perfused retrograde (approximate speed of 10 ml/min) for three minutes. The fixative was then switched to 3% glutaraldehyde and 1½% paraformaldehyde in the same buffer for another four minutes. The cannula was then removed from the aorta and three samples (approximately 3 mm cubes) were removed from different areas of the left ventricular wall and placed in fresh 3% glutaraldehyde and 1½% paraformaldehyde in 0.1M Na cacodylate buffer at pH 7.4. The vials were stored in the refrigerator until they were processed for transmission electron microscopy (at least overnight). The samples were then cut into smaller cubes (1.5 mm) rinsed 3 times in 0.1M Na cacodylate buffer, pH 7.4 with 4% sucrose added, and postfixed for 2 hours with 2% osmium tetroxide, 0.8% potassium ferricyanide, in 0.1M Na cacodylate on ice. The samples were rinsed with water and en bloc stained with saturated aqueous uranyl acetate for two hours at 60° C., followed by dehydration in a graded series of ethanols and then propylene oxide. Following embedding in Spurr resin, silver sections were cut from each of the samples and photographed on a JEOL EM 1200 electron microscope. Starting at the middle of the section on the left side, micrographs of each fiber were taken straight across to the right side. This is possible because one fiber usually runs the entire length of the section.

Conventional statistical methods were used to analyze the data. Student's T test for paired or unpaired comparisons were used to establish a difference between two means, and deemed significant when p=0.05.

Preliminary studies demonstrated that normothermic, global ischemia of isolated rat hearts caused a rapid decrease of the left ventricular pressure and within 6–8 minutes the hearts stopped contracting completely. In parallel to the loss of mechanical activity, an increase in the resting tension, arrhythmia's, and reduction in coronary flow were also observed.

The compounds of the present invention are particularly useful for inhibiting and/or treating the following conditions: reperfusion injury, restenosis, atherosclerotic disease, ventricular tachycardia, ventricular fibrillation, ultrastructural damage, arrhythmia's, myocardial ischemia, asthma, septic shock, ARDS, stroke, vasospasm, head injury, spinal cord injury, endothelial-related respiratory conditions, bacterial meningitis, and inflamed bowel conditions.

The imidazole derivatives of the present invention are also useful for improving mammalian vasomotor tone. The compounds protect the endothelial dependent relaxation factor (EDRF/nitric oxide) cycle from interruption by singlet oxygen and the hydroxyl radical.

The imidazole derivatives of the present invention can be administered by different routes depending on the condition of the patient. Typical modes of administration include, but are not limited to, oral, intravenous, intrathecal and transdermal. Administration can also include surgically implanted devices such as intravascular stents, "weeping" or porous balloons, and polymers (e.g., hydrogel polymers) used in intravascular paving. Alternatively, a therapeutic amount of the imidazole derivative can be carried by a suitable biomaterial, e.g., a liposome. The oral formulations can be made for sustained or immediate release.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material, such as a liposome.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Other suitable carrier materials include for example, gauze and other materials suitable for patch and bandage application, artificial bone and artificial skin materials.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in water-for-injection or in an aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methycellulose, sodium carboxymethylcellulose, and other well-known suspending agents. Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is also possible to administer the imidazole derivatives of the present invention in a time-release formulation. A wide variety of methods are now available in the art for preparing time-release or long-acting compositions. Any of these time-release or long-acting formulations is suitable in the practice of the present invention as long as it does not adversely affect the effectiveness of the imidazole derivatives in the treatment or inhibition of its intended pharmaceutical or biological activity. Advantages of time-release formulations included a lower concentration of peak serum absorption which substantially reduces the adverse side effects and toxicity of the compound administered. In addition, a reduced frequency of administration results in improved patient compliance. A frequency of administration of every 12 or 24 hours would be preferred. In addition, more constant serum concentration of the imidazole derivatives would result, thereby allowing a more consistent relief of symptoms.

In another important aspect of the invention, the imidazole derivatives of the present invention can be used in combination with plasminogen activators such as streptokinase, urokinase and tissue plasminogen activator (tPA), as well as related fibrinolytics such as acylated plasminogen streptokinase activator complex, prourokinase, single chain urokinase, antibody-bound plasminogen activators and hybrid t-PA-urokinase proteins and other so called "third generation" thrombolytics.

Additionally, the imidazole derivatives of the present invention can be used in combination with thrombolytics, adhesion anti-bodies, anti-platelet agents, direct anti-thrombins, antisense nucleotides, other antioxidants, and other biologically active ingredients. The combination of the imidazole derivatives of the present invention with the above compounds may further reduce the damage to jeopardized tissue during reperfusion and during the severe inflammatory response by cells.

The formulations, could, for example, contain 50,000 to 50,000,000 IU/ml of tPA and 25–100 mg of imidazole derivatives in a physiologically acceptable solution which is isotonic with blood. When SOD is used with the imidazole derivatives of the present invention, its concentration could be in the range of 2,000 to 100,000 IU/ml.

PHARMACOLOGICAL TESTING

In vitro Studies of the effect of the subject imidazole analogs on macrophage functions in human cells In order to determine the ability of the subject imidazole analogs to reduce the severity of inflammatory responses, infectious diseases, parasitic conditions, and reperfusion injury, in vitro studies of the following cell-damaging macrophage functions are measured as follows:

In vitro effect of subject imidazole analogs in human peripheral monocytes and whole blood stimulated by a concentration of 100 ng/ml of lipopolysaccharide (LPS), with incubation for 16 hours:

Tumor necrosis factor alpha (TNF-a) release

Interleukin-1 beta (IL-IB) release

Interleukin-1 receptor antagonist (IL-lra)

Interleukin-6

Interleukin-8

Granulocyte-macrophage colony-stimulating factor release (GM-CSF)

Procoagulant (tissue) function

Proliferation antibody assays (T-cell functions):
OKT-3 (CD-3)
phytohemoagglutinin (PHA)
mixed lymphocyte reaction (MLR)

Platelet derived growth factor (PDGF)

Oxidation burst from singlet oxygen ($^1O_2$) and hydroxyl radical (OH).

Adhesion

Superoxide radical

In vitro effect of subject imidazole analogs in human peripheral monocytes and whole blood stimulated by a concentration of 200 mg/ml of Zymosan, with incubation for nineteen (19) minutes:

Platelet activating factor (PAF)

Prostaglandin ($PGE_2$)

Leukotriene ($LTB_4$)

In vitro effect of subject imidazole analogs in human peripheral monocytes and whole blood stimulated by a concentration of $5 \times 10^{-9}$ molar f-Met-Leu-Phe, with incubation for 90 minutes:

Monocyte chemotaxis

In vivo studies of the effect of the subject imidazole compounds on the central nervous system The imidazole derivatives are tested by measuring the volume of cerebral infarction in animals receiving systemic injections of the imidazole derivatives. The experimental approaches, which are described in detail below, provide complementary information regarding the effects of oxygen deprivation on cerebral function. Moreover, they permit quantitative analyses of the effects of therapeutic agents on ischemic brain damage.

The direct participation of free radicals in ischemic neuropathology and the potent ability of imidazole derivatives to scavenge free radicals suggest that the new imidazole derivatives will be neuroprotective. The probability of this positive outcome is further supported by recent studies demonstrating protective effects of imidazole derivatives on free radical-induced damage to myocardium and basilar artery.

DETAILED METHODS

SLICE STUDIES

Electrophysiological responses to transient hypoxia are studied in neocortical brain slices from adult rats. Evoked responses and direct current (DC) potentials are recorded in layer III of the parietal cortex under normoxic and hypoxic conditions. The recovery of evoked synaptic responses and DC potentials are measured for control and imidazole derivative-treated slices. Adult Sprague-Dawley rats weighing 150–200 g are anesthetized with ether and sacrificed by decapitation. The basic procedures for preparing cortical brain slices are similar to those described previously for rat cortex. Briefly, the brains are rapidly removed and placed in cold, artificial cerebrospinal fluid (ACSF). The ACSF consists of the following (in mM): 110.2 NaCl, 2.9 KCl, 1.1 $KH_2PO_4$, 2.1 $MgSO_4$, 1.8 $CaCl_2$, 22.8 $NaHCO_3$, 8.9 glucose. Using a razor blade, the brains are first hemisected at the midline, and then one of the hemispheres is bisected in a horizontal plane followed by a sagittal section. The superior-lateral quadrant of this dissection is placed on a tissue chopper and brain slices are cut in a coranal plane at a thickness of 400 mm. Brains slices containing the parietal cortex at the level of the striatum are placed in a petri dish containing ACSF. Slices are then transferred to a holding chamber held at 35.5° C. and maintained at interface with a humidified atmosphere of 95% $O_2$: 5% $CO_2$ (i.e. normoxic conditions). After a postsacrifice period of at least one hour, slices are transferred to a recording chamber as required.

A bipolar stimulating electrode is positioned under visual guidance near the layer IV—layer V border in the slice. A glass microelectrode filled with 3M NaCl (1–5 megaohm) is placed in layer III above the position of the stimulating electrode. Stimuli are delivered once every fifteen seconds and the amplitude of evoked cortical potentials measured in response to a range of stimulation intensities. During the course of an experiment stimuli are administered at an intensity adjusted to elicit a response of approximately 60% of the minimal amplitude. Hypoxic conditions are achieved by substituting 99% $N_2$ for the normal 95% $O_2$:5% $CO_2$ in the atmosphere of the recording chamber. The standard temperature in the recording chamber is 35.5° C.

A stable baseline of evoked responses is established under normoxic conditions for at least 15 minutes. Imidazole derivative (10 or 100 mM) or standard aCSF is then perfused for the remainder of the experiment. After 15 minutes of perfusion with the imidazole derivative hypoxic conditions are initiated. Hypoxic conditions were maintained until 10 minutes following the occurrence of hypoxic depolarization after which the slices are reoxygenated. Slices are monitored continuously for one hour following reoxygenation.

The potential neuroprotective effect of the imidazole derivatives are determined by comparing the recovery of evoked responses following hypoxia in control and imidazole derivative treated slices.

MCA STUDIES

The experimental approach for focal cerebral ischemia entails reversible occlusion of both carotid arteries and a single middle cerebral artery (MCA) for a period of three hours. This procedure produces consistent and substantial infarction of the rat neocortex ipsilateral to the MCA occlusion. This surgical procedure is in accordance with the guidelines of the National Institutes of Health. The postsurgery survival period is three days. Animals are sacrificed by decapitation under deep anesthesia. The endpoints of these studies are: a) volume of tissue infarction and, b) amount of edema. The volume of tissue infarction is determined by computerized morphometric analysis of TTC-positive and TTC-negative staining in serial, voronal sections of brain. The amount of edema is determined by comparing total neocortial volume in the infarcted and non-infarcted hemispheres of the brain.

Composition of groups: Each experimental group includes 10 animals. A total of 60 animals are examined (i.e., 6 groups of 10 animals). The following groups will be examined.

| GROUPS | 30 min pre | 30 min post | 3 hr post |
|---|---|---|---|
| 1) MCA only | − | − | − |
| 1) MCA + vehicle | − | + | + |
| 2) MCA + vehicle | + | + | + |
| 3) MCA + low dose imidazole derivatives | − | + | + |
| 4) MCA + low dose imidazole derivatives | + | + | + |
| 5) MCA + high dose imidazole derivatives | − | + | + |
| 6) MCA + high dose imidazole derivatives | + | + | + |

INJECTION TIMES (relative to ischemia)

Species: Sprague Dawley Rat (280–320 g)

Drug administration: Injections are administered i.v.

Sacrifice: 3 days postsurgery

Analyses: All sections are coded and the identity of the animal is unknown to the microscopist at the time of analysis. Computer-assisted morphometric analyses are performed to determine the volume of infarction and edema.

Synthesis Procedures for Imidazole Derivatives

I. Preparation of amino-imidazole a. 2 grams nitro-imidazole is dissolved in 100 ml 1,4-dioxane to which 0.8 g [40% (w/v)] 5% Pd/C was added.

b. The solution is mixed 22 hours, room temperature, under a saturated $H_2$ blanket.

c. The catalyst is removed from the solution by filtration (Whatman 42 filter paper), and two successive filtrations yields a bluish-black solution of product.

d. The presence of the amino group is confirmed by ninhydrin spray following TLC in butanol/acetic acid water (90:10:25; Rf 0.24).

e. The amino-imidazole compound is stable in dioxane solution, but rapidly decomposes if taken to dryness.

II. Preparation of N,N'-di(5-imidazolyl) urea a. The solution is placed in a round-bottom flask and 2 grams of urea (dissolved in 50 ml water) is added.

b. 2 mls concentrated HCl and 2 mls glacial acetic acid is added to the solution.

c. the reaction mixture is refluxed overnight.

d. The volume of the solution is reduced under vacuum, methanol is added, and then the solution is taken to dryness by rotary evaporation under reduced pressure with low (40° C.) heat, e. The residue is re-dissolved in methanol to which an excess of diethyl ether is added.

f. The white precipitate that forms is collected by suction filtration and re-dissolved in methanol/water.

g. The solution is concentrated by rotary evaporation and allowed to stant at 4° C.

h. Pale yellow crystals are recovered and washed with cold ether. Yield from 2 grams nitro-imidazole is 370 mg (18.5%). Soluble in methanol water.

Assays for N,N'-bis(5-imidazolyl) urea

UV Spectrum
A small amount of solid was dissolved in methanol:
λ max 225, shoulder 265
Distinct UV spectrum compared with urea or imidazole.
Reverse phase HPLC
HPLC solvent A: 0.1% (v/v) trifluoroacetic acid
HPLC solvent B: 80% (v/v) acetonitrile in 0.1% (v/v) TFA in water
1.0 ml/min., OD 220 nm
0–35 minutes; 5–70% solvent B
C18–5 micron, 4.6×25 cm.
Compound is non-adsorbed to the column and emerges with the solvent front under these conditions.

Other assays

1. Compound is ninhydrin test negative—indicates non-reactive for free amino groups.

2. NMR—ID-1H scan shows presence of imidazole protons.

3. Compound is Pauly test positive—indicates presence of intact imidazole functional group.

III. Alternate Preparation of N,N'-di(5-imidazolyl) urea

A. First synthesis scheme:

12.21 μmol of 5-aminoimidazole (prepared from nitroimidazole under hydrogenation conditions) was mixed with 6.1 μmol carbonyldiimidazole in 50% dioxane/water solution, pH 6.5. The extent of reaction was monitored by ninhydrin colorimetric assay, but overnight, there was no significant decrease in ninhydrin reactivity. The carbonyldiimidazole concentration was increased to 9 μmol total and the reaction was allowed to proceed for another 12 hours at room temperature.

The ninhydrin colorimetric assay indicated 50% decrease and a new UV spot was observed on thin layer chromatography in two different solvent systems and on analytical reverse-phase HPLC.

The reaction solvents were removed by rotary evaporation under reduced pressure, but upon concentration, the constituents (probably unreacted amine) began decomposition to yield a black char. Further separation of products and reactants was deemed unfeasible and so the procedure was stopped at this step.

B. Second synthesis scheme:

218 μmol aminoimidazole in dioxane was placed in a two-necked round bottom flask to which 50 ml water was added. The reaction mixture was cooled to 10° C. and 120 μmol phosgene in toluene was added by dropping funnel. After phosgene addition the reaction was allowed to come to room temperature and mixed overnight. There was no change in ninhydrin reactivity and so another 100 μmol phosgene was added, again with no obvious reaction taking place. Because water was added inadvertantly to this reaction mixture, it was decided that hydrolysis was a serious competing reaction, and so the phosgene concentration was increased to excess over the aminoimidazole.

Reaction overnight produced a decrease in ninhydrin. The reaction mixture was twice extracted with ethyl acetate, dried over sodium sulfate, taken to dryness under reduced pressure, and analyzed by 1H-NMR for the presence of the product. None was found.

The aqueous phase was subjected to preparative reverse-phase HPLC and two UV absorbing peaks were identified, separated, lyophilized, and a portion again subjected to NMR. Although the starting material was found in the aqueous phase, none of the desired product was isolated.

IV. Preparation of 1,5-di(5-imidazoyl) pentane

This is a stepwise synthesis using material obtained at each of the individual steps to accomplish the next step of the synthesis. The procedure followed is based on the published procedure outlined in the Journal fur praktishche Chemie, volume 4, pages 132–142, 1964, by Schubert, Wallwitzm, and Koch, as deciphered from the original German.

a. Preparation of 1,5-azoacetylpentane 7.6 μmol of pimeloyl chloride was converted to the corresponding 1,7 diazo compound using diazomethane generated in situ from diazad according to standard procedures. Analytical HPLC of the reaction mixture showed the disappearance of pimeloyl chloride with the appearance of the desired product.

b. Preparation of the dibromo compound; 1,5-bromoacetyl-pentane

The solution was warmed to room temperature and Hbr solution (33% in acetic acid) was added. After a total addition of 10.3 μmol Hbr, the solution was reduced in volume under reduced pressure, and the reaction was run for another 8 hours at room temperature with stirring.

c. Preparation of the diamino compound: 1,5-aminoacetyl-pentane

The above solution was cooled to −20° Cm and ammonia gas was bubbled through the solution to saturation (note; this is a change from the published procedure). The reaction was monitored by means of the ninhydrin colorimetric assay, and the product was quantitated using the same assay.

d. Cyclization of the compound

Based on the concentration of the aminocompound, 160 mg KSCN was added and the solution was heated for a total of 7 hours after which ninhydrin assay revealed the disappearance of the amine with the concomitant appearance of a new UV absorbing peak on HPLC and TLC. This product needs to be isolated by prep. HPLC before continuing.

e. Removal of the thiol group

The thiol group will be removed from the 2-position of the imidazole ring using Rainey nickel reduction.

The invention will be more fully described in conjunction with the following specific examples which are not to be construed as limiting the scope of the invention.

EXAMPLE 1

Hard gelatin capsules are prepared using the following ingredients:

|  | Quantity (mg/capsule) |
| --- | --- |
| N,N,'Diimidazolyl Urea | 250 |
| Starch dried | 200 |
| Magnesium stearate | 10 |

The above ingredients are mixed and filled into hard gelatin capsules in 460 mg quantities.

EXAMPLE 2

A tablet formula is prepared using the ingredients below:

|  | Quantity (mg/tablet) |
| --- | --- |
| N,N'-Di(5-imidazolyl) Urea | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 3

Tablets each containing 60 mg of active ingredients are made up as follows:

| 1,5-Di(5-imidazolyl)pentane | 60 mg |
| --- | --- |
| Starch | 45 mg |
| Microcrystalline cellulose | 35 mg |
| Polyvinylpyrrolidone | ? |
| (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 4

Capsules each containing 80 mg of medicament are made as follows:

| N,N'-Di(5-imidazolyl) Urea | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No./45 mesh U.S. sieve and filled into hard gelatin capsules in 200 mg quantities.

EXAMPLE 5

Suspensions each containing 50 mg of medicament per 5 ml dose are made as follows:

| 1,5(5-imidazoyl) pentane | 50 mg |
| --- | --- |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 6

Capsules each containing 150 mg of medicament are made as follows:

| | |
|---|---|
| Di(5-imidazolyl methyl)ketone | 150 mg |
| Starch | 164 mg |
| Microcrystalline cellulose | 164 mg |
| Magnesium stearate | 22 mg |
| Total | 500 mg |

The active ingredients, cellulose, starch and magnesium stearate are blended, passed through a No. 45 mesh U.S. sieve, and filled into hard gelatin capsules in 500 mg quantities.

While the invention has been described in terms of its preferred embodiments, those skilled in the art will recognize that the invention can be practiced with modification within the spirit and scope of the appended claims.

Having thus described our invention, what we claim as new and desire to secure by later patent is a follows:

1. A method for inhibiting or treating reperfusion injury in a mammalian organism in need of such treatment, said method comprising administering to said mammal an amount of an imidazole derivative effective in the inhibition or treatment of reperfusion injury, said imidazole derivative having the formula:

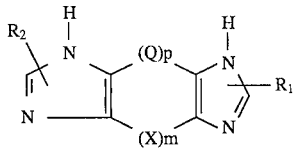

wherein $R_1$ and $R_2$ are selected from the group consisting of hydrogen and normal, secondary, branched and tertiary $C_{1-18}$ alkyl groups; X is a heteroatom selected from the group consisting of oxygen and sulfur; Q is selected from the group consisting of $—(CH_2)—_n$, $—(CH)—_n$

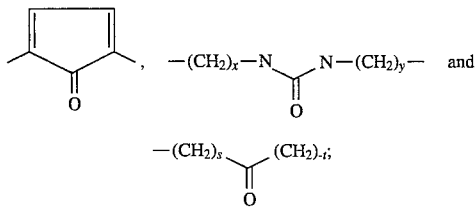

and
m=0 or 1
p=0 or 1  n=1–18
x=y=0–3
s=1–3
t=1–3
with the proviso that when p=0 then m=1 and the imidazole rings are joined together by a single bond to make a fused tricyclic ring, and when m=0 then p=1.

2. The method of claim 1 wherein said imidazole derivative is N,N'-di(5-imidazolyl) urea.

3. The method of claim 1 wherein said imidazole derivative is di(5-imidazoyl methyl) ketone.

4. The method of claim 1 wherein said imidazole derivative is bis 2,3–4,5 imidazo furan.

5. The method of claim 1 wherein said imidazole derivative is 2,5-di(-5-imidazolyl) cyclopentadien-1-one.

6. The method of claim 1 wherein said imidazole derivative is 1,2-di(5-imidazolyl) ethane.

7. A method of controlling at least one of ventricular tachycardia, ventricular fibrillation, and ultrastructural damage to or infarction of coronary and cardiac tissue, comprising the step of providing to said tissue an amount of an imidazole derivative effective to prevent tachycardia or fibrillation, ultrastructural damage to or infarction of said tissues, said imidazole derivative having the formula:

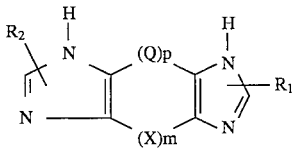

wherein $R_1$ and $R_2$ are selected from the group consisting of hydrogen and normal, secondary, branched and tertiary $C_{1-18}$ alkyl groups; X is a heteroatom selected from the group consisting of oxygen and sulfur; Q is selected from the group consisting of $—(CH_2)—_n$, $—(CH)—_n$

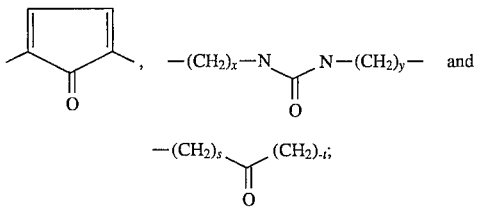

and
m=0 or 1
p=0 or 1
n=1–18
x=y=0–3
s=1–3
t=1–3
with the proviso that when p=0 then m=1 and the imidazole rings are joined together by a single bond to make a fused tricyclic ring, and when m=0 then p=1.

8. The method of claim 7 wherein said imidazole derivative is N,N' di(5-imidazolyl) urea.

9. The method of claim 7 wherein said imidazole derivative is di(5-imidazolyl methyl) ketone.

10. The method of claim 7 wherein said imidazole derivative is bis 2,3–4,5 imidazo furan.

11. The method of claim 7 wherein said imidazole derivative is 2,5 di(-5-imidazolyl) cyclopentadien-1-one.

12. The method of claim 7 wherein said imidazole derivative is 1,2 di(5-imidazolyl) ethane.

13. A method for treating runaway inflammatory responses in a mammalian organism in need of such treatment, said method comprising administering to said mammal an effective amount of an imidazole derivative having the formula:

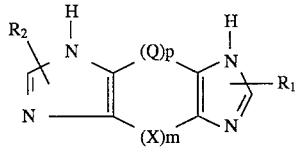

wherein $R_1$ and $R_2$ are selected from the group consisting of hydrogen and normal, secondary, branched and tertiary $C_{1-18}$ alkyl groups; X is a heteroatom selected from the group consisting of oxygen and sulfur; Q is selected from the group consisting of $—(CH_2)—_n$, $—(CH)—_n$

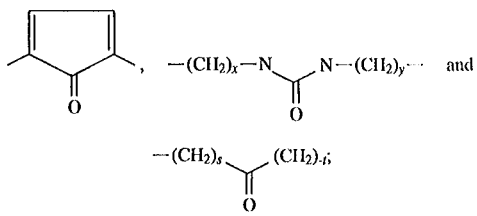

and
m=0 or 1
p=0 or 1
n=1–18
x=y=0–3
s=1–3
t=1–3 with the proviso that when p=0 then m=1 and the imidazole rings are joined together by a single bond to make a fused tricyclic ring, and when m=0 then p=1.

14. The method of claim 13 wherein said imidazole derivative is N,N' di(5-imidazolyl) urea.

15. The method of claim 13 wherein said imidazole derivative is di(5-imidazolyl methyl) ketone.

16. The method of claim 13 wherein said imidazole derivative is bis 2,3-4,5 imidazo furan.

17. The method according to claim 13, wherein the runaway inflammatory conditions are selected from heart attack, stroke, subarachnoid hemorrhage, head injury, spinal cord injury, burns, wounds, asthma, septic shock, adult respiratory distress syndrome, bacterial meningitis and inflammatory bowel conditions and further wherein said imidazole derivatives inhibit tissue damage caused by cytokines and growth factors from runaway inflammatory condition and chemotactic cascades produced during surgical procedures.

18. The method of claim 17 wherein said imidazole derivative is N,N'-di(5-imidazolyl) urea.

19. The method of claim 13 wherein said imidazole derivative is 2,5 di(-5-imidazolyl) cyclopentadien-1-one.

20. The method of claim 13 wherein said imidazole derivative is 1,2 di(5-imidazolyl) ethane.

21. The method of claim 17 wherein said imidazole derivative is di(5-imidazoyl methyl) ketone.

22. The method of claim 17 wherein said imidazole derivative is bis 2,3-4,5 imidazo furan.

23. The method of claim 17 wherein said imidazole derivative is 2,5-di(-5-imidazolyl) cyclopentadien-1-one.

24. The method of claim 17 wherein said imidazole derivative is 1,2-di(5-imidazolyl) ethane.

25. A method of preventing, controlling, or ameliorating the growth of undesired or abnormal tissue that occurs in a mammal following surgical procedures, said method comprising the step of administering a therapeutically effective amount of an imidazole derivative having the formula:

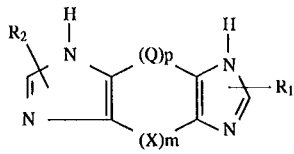

wherein $R_1$ and $R_2$ are selected from the group consisting of hydrogen and normal, secondary, branched and tertiary $C_{1-18}$ alkyl groups; X is a heteroatom selected from the group consisting of oxygen and sulfur; Q is selected from the group consisting of $—(CH_2)—_n$, $—(CH)—_n$

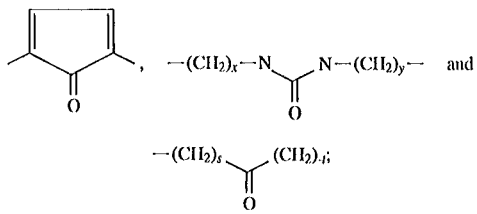

and
m=0 or 1
p=0 or 1
n=1–18
x=y=0–3
s=1–3
t=1–3 with the proviso that when p=0 then m=1 and the imidazole rings are joined together by a single bond to make a fused tricyclic ring, and when m=0 then p=1.

26. The method of claim 25 wherein the growth of undesired or abnormal tissue results from at least one of retenosis following angioplasty and atherosclerotic plaque within a vessel.

27. The method of claim 25 wherein the vessel comprises a man-made vascular graft.

28. The method of claim 25 wherein said imidazole derivative is N,N'-di(5-imidazolyl) urea.

29. The method of claim 25 wherein said imidazole derivative is di(5-imidazolyl methyl) ketone.

30. The method of claim 25 wherein said imidazole derivative is bis 2,3-4,5 imidazo furan.

31. The method of claim 25 wherein said imidazole derivative is 2,5-di(-5-imidazolyl) cyclopentadien-1-one.

32. The method of claim 25 wherein said imidazole derivative is 1,2-di(5-imidazolyl) ethane.

33. A method of ameliorating damage to mammalian central nervous system tissue, cells, or vessels, comprising the step of administering to a mammalian subject in need thereof an effective amount of an imidazole derivative having the formula:

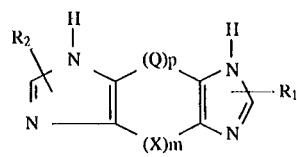

wherein $R_1$ and $R_2$ are selected from the group consisting of hydrogen and normal, secondary, branched and tertiary $C_{1-18}$ alkyl groups; X is a heteroatom selected from the group consisting of oxygen and sulfur; Q is selected from the group consisting of $—(CH_2)—_n$, $—(CH)—_n$

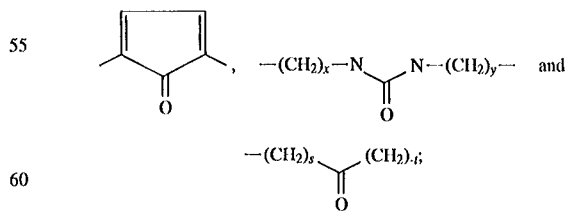

s=1-3
t=1-3
with the proviso that when p=0 then m=1 and the imidazole rings are joined together by a single bond to make a fused tricyclic ring, and when m=0 then p=1.

34. The method of claim 33 wherein said imidazole derivative is N,N'-di(5-imidazolyl) urea.

35. The method of claim 33 wherein said imidazole derivative is di(5-imidazoyl methyl) ketone.

36. The method of claim 33 wherein said imidazole derivative is bis 2,3-4,5 imidazo furan.

37. The method of claim 33 wherein said imidazole derivative is 2,5-di(-5-imidazolyl) cyclopentadien-1-one.

38. The method of claim 33 wherein said imidazole derivative is 1,2-di(5-imidazolyl) ethane.

39. A method of protecting mammalian tissue and cells from damaging oxygen species by administering to a mammalian subject in need thereof an effective amount of an imidazole derivative to scavenge at least one of singlet oxygen and hydroxyl radicals, said imidazole derivative having the formula:

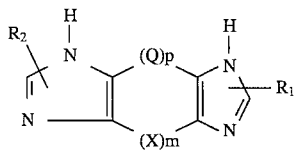

wherein $R_1$ and $R_2$ are selected from the group consisting of hydrogen and normal, secondary, branched and tertiary $C_{1-18}$ alkyl groups; X is a heteroatom selected from the group consisting of oxygen and sulfur; Q is selected from the group consisting of $-(CH_2)-_n$, $-(CH)-_n$

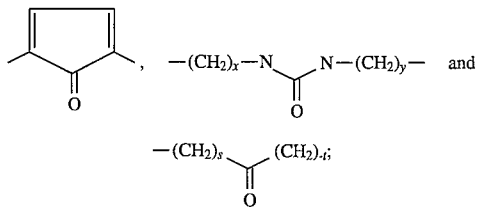

and
m=0 or 1
p=0 or 1
n=1-18
x=y=0-3
s=1-3
t=1-3
with the proviso that when p=0 then m=1 and the imidazole rings are joined together by a single bond to make a fused tricyclic ring, and when m=0 then p=1.

40. A method of improving mammalian vasomotor tone by administering to a mammal an amount of an imidazole derivative sufficient to protect the endothelial dependent relaxation factor (EDRF/nitric oxide) cycle, said imidazole derivative having the formula:

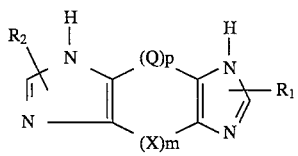

wherein $R_1$ and $R_2$ are selected from the group consisting of hydrogen and normal, secondary, branched and tertiary $C_{1-18}$ alkyl groups; X is a heteroatom selected from the group consisting of oxygen and sulfur; Q is selected from the group consisting of $-(CH_2)-_n$, $-(CH)-_n$

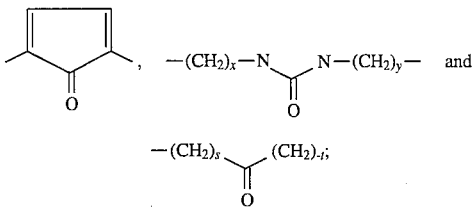

and
m=0 or 1
p=0 or 1
n=1-18
x=y=0-3
s=1-3
t=1-3
with the proviso that when p=0 then m=1 and the imidazole rings are joined together by a single bond to make a fused tricyclic ring, and when m=0 then p=1.

41. The method of claim 40 wherein said imidazole derivative is N,N'-di(5-imidazolyl) urea.

42. The method of claim 40 wherein said imidazole derivative is di(5-imidazoyl methyl) ketone.

43. The method of claim 40 wherein said imidazole derivative is bis 2,3-4,5 imidazo furan.

44. The method of claim 40 wherein said imidazole derivative is 2,5-di(-5-imidazolyl) cyclopentadien-1-one.

45. The method of claim 40 wherein said imidazole derivative is 1,2-di(5-imidazolyl) ethane.

46. A pharmaceutical composition useful for inhibiting damage to jeopardized tissue during reperfusion in a mammal which comprises: (a) a compound of the formula

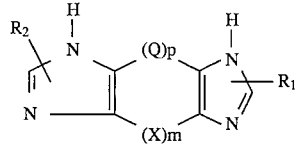

wherein $R_1$ and $R_2$ are selected from the group consisting of hydrogen and normal, secondary, branched and tertiary $C_{1-18}$ alkyl groups; X is a heteroatom selected from the group consisting of oxygen and sulfur; Q is selected from the group consisting of $-(CH_2)-_n$, $-(CH)-_n$

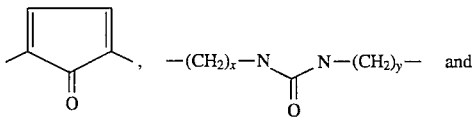

and
m=0 or 1
p=0 or 1
n=1-18
x=y=0-3
s=1-3
t=1-3
with the proviso that when p=0 then m=1 and the imidazole rings are joined together by a single bond to make a fused tricyclic ring, and when m=0 then p=1; (b) a therapeutic agent selected from the group consisting of urokinase, streptokinase, tissue plasminogen activator and superoxide dismutase; and (c) a pharmaceutically acceptable inert carrier.

47. A therapeutic composition for treating reperfusion injury and injury due to severe inflammatory responses in a mammal which comprises: (a) a compound of the formula

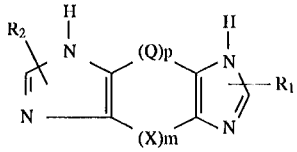

wherein $R_1$ and $R_2$ are selected from the group consisting of hydrogen and normal, secondary, branched and tertiary $C_{1-18}$ alkyl groups; X is a heteroatom selected from the group consisting of oxygen and sulfur; Q is selected from the group consisting of $-(CH_2)-_n$, $-(CH)-_n$

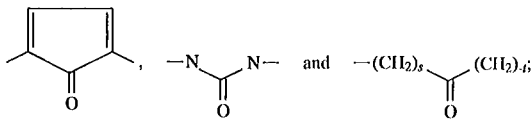

and
m=0 or 1
p=0 or 1
n=1–18
s=1–3
t=1–3
with the proviso that when p=0 then m=1 and the imidazole rings are joined together by a single bond to make a fused tricyclic ring, and when m=0 then p=1; and (b) a carrier which is a biomaterial or a delivery device for direct or indirect delivery to tissue or cells in need of treatment.

48. The composition of claim 47 wherein (b) comprises liposomes timed-release capsules or tablets, hydrogel or other polymers, gels, gauzes, patches, bandages, materials suitable for artificial skin and bone, drug delivery catheters, stents, osmotic pumps, metered dose inhalers nebulizers, and aerosolizers.

49. A compound of the formula:

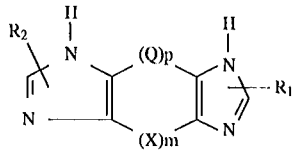

wherein $R_1$ and $R_2$ are selected from the group consisting of hydrogen and normal, secondary, branched and tertiary $C_{1-18}$ alkyl groups; X is a heteroatom selected from the group consisting of oxygen and sulfur; Q is selected from the group consisting of $-(CH)-_n$

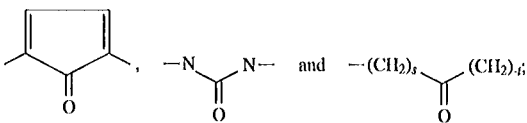

and
m=0 or 1
p=0 or 1
n=1–18
s=1–3
t=1–3
with the proviso that when p=0 then m=1 and the imidazole rings are joined together by a single bond to make a fused tricyclic ring, and when m=0 then p=1.

50. The compound of claim 49 wherein said imidazole derivative is di(5-imidazolyl methyl) ketone.

51. The compound of claim 49 wherein said imidazole derivative is bis 2,3–4,5 imidazo furan.

52. The compound of claim 49 wherein said imidazole derivative is N,N' di(5-imidazolyl) urea.

53. The compound of claim 49 wherein said imidazole derivative is 2,5 di(-5-imidazolyl) cyclopentadien-1-one.

* * * * *